(12) United States Patent
Dale et al.

(10) Patent No.: US 9,168,135 B2
(45) Date of Patent: Oct. 27, 2015

(54) DEVICE FOR COLLAPSING AND LOADING A HEART VALVE INTO A MINIMALLY INVASIVE DELIVERY SYSTEM

(71) Applicant: St. Jude Medical, Cardiology Division, Inc., St. Paul, MN (US)

(72) Inventors: Theodore Paul Dale, Corcoran, MN (US); Aaron J. Chalekian, Savage, MN (US); Valerie J. Glazier, Eden Prairie, MN (US); Huisun Wang, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/610,222

(22) Filed: Jan. 30, 2015

(65) Prior Publication Data
US 2015/0135647 A1  May 21, 2015

Related U.S. Application Data

(62) Division of application No. 13/211,484, filed on Aug. 17, 2011, now Pat. No. 9,021,670.

(60) Provisional application No. 61/374,429, filed on Aug. 17, 2010.

(51) Int. Cl.
*A61F 2/95* (2013.01)
*A61F 2/24* (2006.01)

(52) U.S. Cl.
CPC .............. *A61F 2/2427* (2013.01); *A61F 2/2418* (2013.01); *A61F 2002/9522* (2013.01); *Y10T 29/49927* (2015.01)

(58) Field of Classification Search
CPC ................. A61F 2/2427; A61F 2/2418; A61F 2002/9522; Y10T 29/49927

USPC ............ 29/244, 278, 255, 257, 261, 268, 276; 81/90.3, 92, 98, 420, 424.5, 426.5; 72/274, 276, 467; 600/37; 623/2.11
See application file for complete search history.

(56) References Cited

U.S. PATENT DOCUMENTS 5,437,083 A   8/1995   Williams et al.
5,725,519 A   3/1998   Penner et al.
(Continued)

FOREIGN PATENT DOCUMENTS

EP   0941713 A1    9/1999
WO   2011150399 A1  12/2011

OTHER PUBLICATIONS

International Search Report and Written Opinion for Application No. PCT/US2011/001445 dated Apr. 19, 2012.

*Primary Examiner* — David Bryant
*Assistant Examiner* — Steven A Maynard
(74) *Attorney, Agent, or Firm* — Lerner, David, Littenberg, Krumholz & Mentlik, LLP

(57) ABSTRACT

A device is provided for collapsing a stented bioprosthetic valve, including first section and second sections, each spanning between first and second ends of the device. The second section of the device is associated with the first section to at least partially enclose an internal cavity formed by the first and second sections, the internal cavity tapering from an open insertion portion at a first end of the device to an open exit portion at a second end of the device. The insertion portion has a larger dimension than the exit portion. When the first section and second section are substantially enclosing the internal cavity, a stented bioprosthetic valve may be inserted into the insertion portion and collapsed as it is moved toward and through the exit portion. The valve may then be loaded on an apparatus for insertion into the body.

16 Claims, 20 Drawing Sheets

(56) References Cited

U.S. PATENT DOCUMENTS

| | | |
|---|---|---|
| 5,810,873 A | 9/1998 | Morales |
| 5,992,000 A | 11/1999 | Humphrey et al. |
| 6,068,635 A | 5/2000 | Gianotti |
| 6,514,285 B1 * | 2/2003 | Pinchasik .................... 623/1.22 |
| 6,702,845 B1 | 3/2004 | Cully et al. |
| 6,925,847 B2 | 8/2005 | Motsenbocker |
| 7,096,554 B2 * | 8/2006 | Austin et al. .................... 29/282 |
| 7,316,147 B2 * | 1/2008 | Perreault et al. ................ 72/402 |
| 7,636,997 B2 * | 12/2009 | Perreault et al. ................ 29/508 |
| 7,926,320 B2 * | 4/2011 | Perreault et al. ................ 72/402 |
| 7,993,394 B2 * | 8/2011 | Hariton et al. ............... 623/2.17 |
| 8,012,402 B2 * | 9/2011 | Kleiner et al. ................ 264/528 |
| 2003/0139795 A1 | 7/2003 | Olson |
| 2009/0093876 A1 | 4/2009 | Nitzan et al. |
| 2009/0292347 A1 * | 11/2009 | Asmus et al. ................ 623/1.11 |
| 2010/0057185 A1 | 3/2010 | Melsheimer et al. |

* cited by examiner

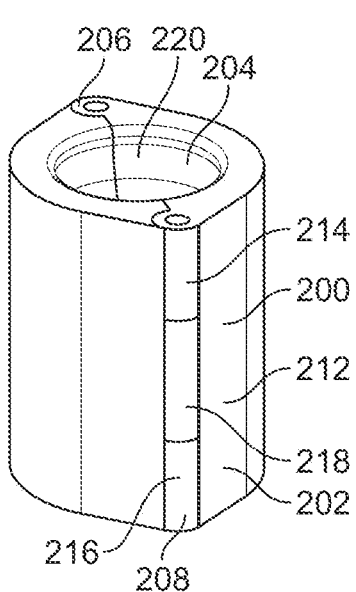
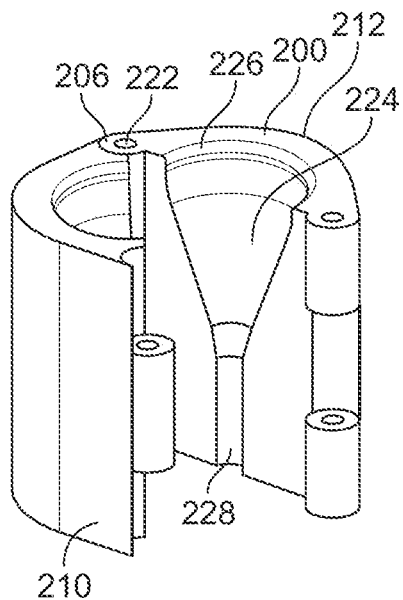
FIG. 2    FIG. 3
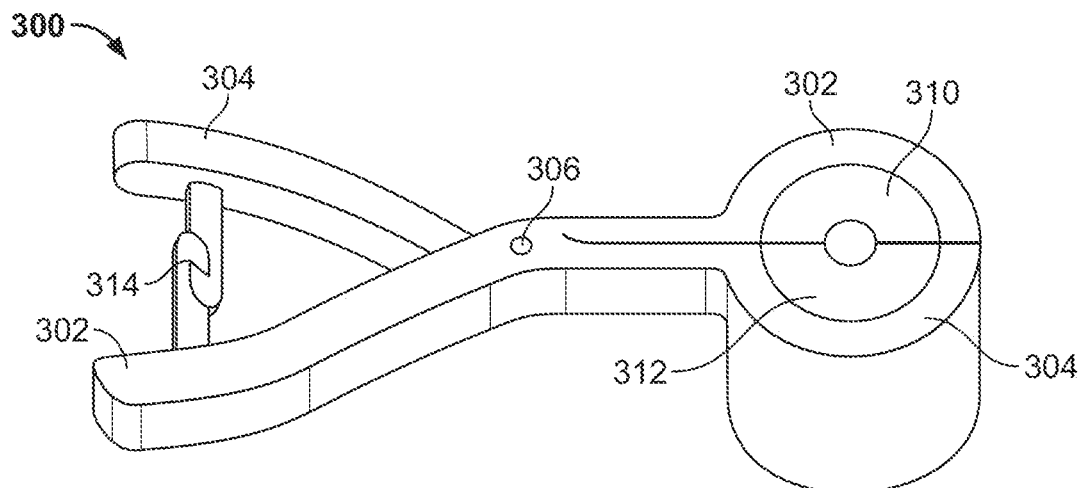
FIG. 4A
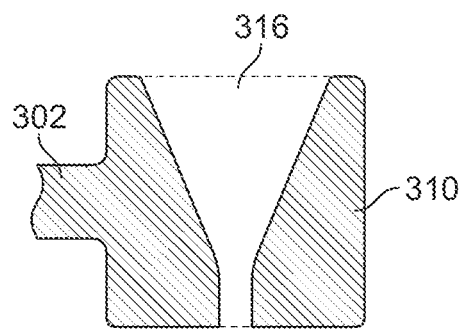
FIG. 4B

DEVICE FOR COLLAPSING AND LOADING A HEART VALVE INTO A MINIMALLY INVASIVE DELIVERY SYSTEM

CROSS-REFERENCE TO RELATED APPLICATIONS

The present application is a divisional of U.S. patent application Ser. No. 13/211,484, filed Aug. 17, 2011, which claims the benefit of the filing date of U.S. Provisional Application No. 61/374,429, filed Aug. 17, 2010, the disclosure of which is hereby incorporated by reference herein.

BACKGROUND OF THE INVENTION

Heart valve disease, and particularly aortic heart valve disease, is a medical problem afflicting many individuals throughout the world. Over time, natural heart valves may leak causing aortic insufficiency or regurgitation. They may also become blocked or exhibit limited function due to aortic stenosis. Among the treatment options for either condition is the destruction of the native valve and insertion of a prosthetic valve through a transapical approach using a minimally invasive delivery device.

Prosthetic valves may be formed from biological materials such as harvested bovine valves or pericardium tissue. Such valves are typically fitted within, and form a portion of, a biologically compatible stent, which may be inserted into the heart at the annulus of the compromised native valve to replace the native valve. For such insertion, it is often necessary to compress the stent to a reduced diameter for loading onto the delivery device and for insertion into the body, whereupon it may be expanded.

In the case of valves formed with biological materials, the stented valve is preferably preserved in the open condition for storage as compression of the valve material for extended periods compromises the integrity of the biological valve. It is therefore necessary to crimp the valve, or reduce its diameter for use in the insertion device, in the operating arena.

SUMMARY OF THE INVENTION

Present crimping devices and methods for collapsing a stented valve have proven to be unsatisfactory as they include bulky devices, are difficult to master, are time consuming, impart undue stress on the stented valve, or include other undesirable qualities. Such devices include direct radial devices, as are well known in the art. It would therefore be beneficial to provide devices and methods for collapsing a stented bioprosthetic heart valve using apparatuses and techniques that overcome the deficiencies of conventional devices. Preferably, such devices and methods may also assist with loading of the collapsed stented valve onto a minimally invasive delivery device.

One embodiment of a device that solves the deficiencies of the prior art includes a device for collapsing a stented bioprosthetic valve, the device having a first end and an opposed second end, a first section spanning between the first and second ends, a second section spanning between the first and second ends, the second section associated with the first section to at least partially enclose an internal cavity formed by the first and second sections. The internal cavity may taper from an open insertion portion at a first end of the device to an open exit portion at a second end of the device, the insertion portion having a larger dimension than the exit portion. When the first section and second section are substantially enclosing the internal cavity, a stented bioprosthetic valve may be inserted into the insertion portion and collapsed as it is moved towards the exit portion. As will be discussed, the valve may be moved with various pushers or tethers.

The first section and second section may fully enclose the internal cavity.

The device may further comprise a tether or pusher adapted to associate with the stented bioprosthetic valve to enable the valve to travel from the insertion portion to the exit portion via the tether or the pusher.

The first section and the second section may be movable between a first position at least partially enclosing the internal cavity and a second position wherein the cavity is fully exposed.

The device may further comprise a collar adapted to fit around at least a portion of the collapsed stented bioprosthetic valve. The collar may include three sections, with a middle of the three sections being raised to form opposed shoulders. The collar may also include an orientation portion to align the collar on a second device. The orientation portion may feature a tab.

The first section may be filled with a heat retaining gel. Similarly, the second section may as well.

The device may further comprise insulation associated with the first section. The second section may also include insulation.

The first section may be manufactured from a high heat capacity metal. The second may as well.

The sections of the device may all be filled with heat retaining gel, may all include insulation, and may all be manufactured from a high heat capacity metal.

The device may further comprising a sleeve insertable into the internal cavity to reduce the volume thereof.

In accordance with certain methods of the present invention, a method of loading a stented bioprosthetic valve onto a minimally invasive delivery system is disclosed. The method includes, in no particular order, the step of crimping the stented bioprosthetic valve from a first condition having a first diameter to a second condition having a second diameter, the second diameter smaller than the first diameter, the crimping being achieved by advancing the stented bioprosthetic valve through a device having a tapered internal cavity, the taper advancing from a first dimension to a second dimension, the second dimension being smaller than the first. Another step includes inserting the stented bioprosthetic valve into a collar. Finally, another step includes loading the collar and the bioprosthetic valve onto a minimally invasive delivery system by threading at least a portion of the system into the collar.

Inserting of the stented bioprosthetic valve into a collar may be performed after crimping.

Inserting of the stented bioprosthetic valve into a collar may be performed simultaneously with at least a portion of the crimping.

The method may also include cooling the device.

The device used in the method may be comprised of an outer structural shell filled with a cold-sustaining gel.

The device may also include an insulating exterior component.

In another embodiment of the invention, a device for collapsing a stented bioprosthetic valve comprises a cavity shaped as a frustoconical funnel spilling into a cylinder, wherein a stented bioprosthetic valve may be passed through the device to collapse the valve.

The device may be configured from high heat capacity metal.

The device may include a cold-retaining gel core.

The device may further comprise a pusher for pushing the stented bioprosthetic valve through the device or tethers for pulling the stented bioprosthetic valve through the device.

The pusher may include cantilevered fingers.

The pusher may include a plurality of telescoping sections, where each section is physically smaller than the previous section as the pusher telescopes.

BRIEF DESCRIPTION OF THE DRAWINGS

The subject matter regarded as the invention is particularly pointed out and distinctly claimed in the concluding portion of the specification. The invention, however, both as to organization and method of operation, together with the features, objects, and advantages thereof, may best be understood by reference to the following detailed description of preferred embodiments when read with the accompanying drawings in which:

FIG. 2 depicts perspective view of a device for collapsing and loading a stented valve onto a minimally invasive delivery system in accordance with certain aspects of the present invention, the device being in a closed condition;

FIG. 3 depicts a perspective view of the device of FIG. 2 in an open position;

FIG. 4A depicts a perspective view of a device for collapsing and loading a stented valve onto a minimally invasive delivery system in accordance with further aspects of the present invention;

FIG. 4B depicts a cross-sectional view of a portion of the device of FIG. 4A;

DETAILED DESCRIPTION

Figure 1:
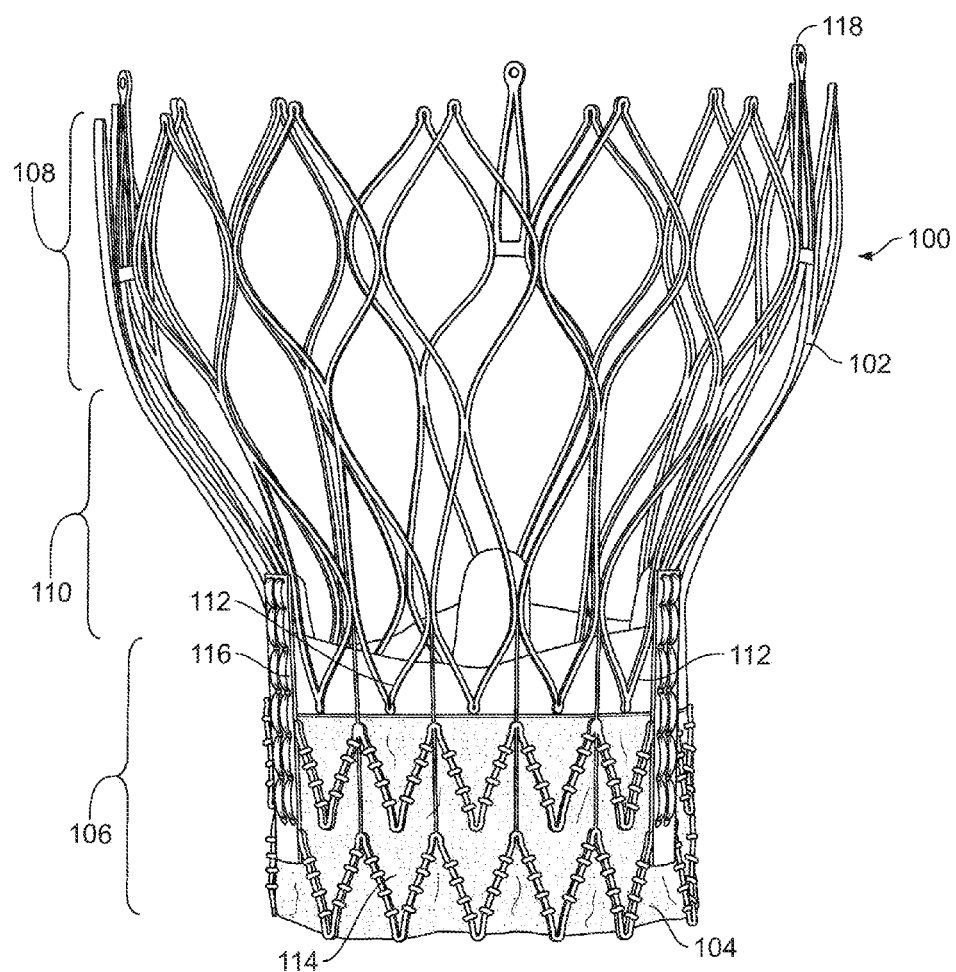
FIG. 1 depicts a conventional bioprosthetic stented valve, as known in the art.

In the following detailed description, preferred embodiments of a device for collapsing and loading a stented bioprosthetic valve (also referred to as a stented valve) onto a minimally invasive delivery system are described in accordance with the present invention. In describing the embodiments illustrated in the drawings, specific terminology may be used for the sake of clarity. However, the invention is not intended to be limited to the specific terms so selected, and it is to be understood that specific terms may also include technical equivalents that operate in a similar manner to accomplish a similar purpose. Where like elements have been depicted in multiple embodiments, identical reference numerals have been used in the multiple embodiments for ease of understanding.

Referring to FIG. 1, there is shown a conventional bioprosthetic stented valve 100. When installed in the heart, the stented valve 100 is positioned at the annulus of the compromised native valve such that there are "upstream" and "downstream" directions relative to blood flow through the heart. These directions are labeled in the figure, and it is to be understood that when viewed in the configuration of FIG. 1, blood flow through the stented valve 100 would be in the upward direction.

As known in the art, the stented valve 100 is typically formed from a unitary element, referred to as a stent 102, with a valve 104 internally connected to the stent. The stent 102 may be formed from many biocompatible materials, and is preferably formed from plastically deformable biocompatible material. Moreover, the stent 102 may be self-expanding or may require the influence of expansion mechanisms, such as balloons, to expand from a compressed condition to an expanded condition. For purposes of the present disclosure, the stent 102 will be hereinafter described as a self-expanding stent. In certain embodiments, the stented valve 100 may expand at temperatures in the range of 45° F. and above, such that reduced temperatures of approximately 0° F. to 45° F. cause the valve to contract, or at least resist contraction less than if at an elevated temperature. Such valves may be constructed of Nitinol or other memory metal.

The valve 104 itself is typically formed from biological materials such as harvested bovine valves or pericardium tissue. For purposes of this disclosure, the valve 104 will be described as a pericardium tissue valve. The valve may also be formed from bioprosthetic materials.

In its relaxed, undeformed room-temperature condition, the self-expanding stent 102 is generally in the form of a body of revolution about an axis, where the body has varying diameter. In a first section, referred to as an annulus section 106, the stent 102 is generally cylindrical and is of a comparatively small diameter. Spaced at the extreme "downstream" position from the annulus section 106 is a second section, referred to as the aortic section 108. The aortic section 108 is generally flared outwardly in the "downstream" direction so as to expand slightly in diameter toward the "downstream" direction. Between the annulus section 106 and the aortic section 108, and connecting the two, is a sinus section 110. The sinus section 110 matches both the "downstream" diameter of the annulus section 106 and "upstream" diameter of the aortic section 108, respectively, at its two ends. As such, it will be appreciated that the sinus section 110 itself typically flares outwardly from the annulus section 106 to the aortic section 108 in a frustoconical manner.

The valve 104 is connected to the stent 102 generally within the annulus section 106, but may extend slightly into the sinus section 110. Conventionally, the valve 104 includes a plurality of leaflets 112, typically either two or three, and a cuff 114. In this example, the leaflets 112 and cuff 114 are all formed from animal pericardium tissue. The cuff 114 extends around the interior of the annulus section 106 of the stent 102 and may be secured to the stent by sutures (not shown) or other attachment mechanisms. In turn, the leaflets 112 are secured to one another and to the cuff 114 at commissure lines 116. The valve leaflets 112 are arranged to permit one-way flow in the "downstream" direction, and alternate between an open condition to allow flow and a closed position to restrict flow. It will be appreciated that the leaflets are inherently in the closed position, such that they reciprocate to the open condition based on the pressurized flow of blood, only to reverse back to a closed condition upon a reduction of such pressure.

It will be appreciated that certain stented valves 100 include eyelets 118 at points along the extreme "downstream" end of the aortic section 108 and extreme "upstream" end of the annulus section 106. The eyelets 118 are typically designed for use in loading the stented valve 100 onto a delivery catheter, in particular for grasping and alignment purposes. However, the eyelets 118 may also be utilized to collapse the stented valve 100, as will be discussed.

The entire stented valve 100 is preferably preserved in its expanded or open condition for storage as the bioprosthetic valve 104 may be compromised by storage in a compressed condition for extend periods of time. As such, it is necessary to crimp the stented valve 100 into a collapsed or reduced diameter condition for use in the surgical installation procedure as soon before the procedure as possible. In order to effectively limit the time period the stented valve 100 is collapsed, the crimping process is conducted in the operating arena by the surgeon or surgical assistants using a specialized device.

FIG. 2 depicts a perspective view of such a specialized crimping device 200 in accordance with a first embodiment of the present invention, the device being in the closed condition. As shown, the crimping device 200 features a generally cylindrical exterior 202 with an annular space defining an internal bore or cavity 204. The crimping device 200 shown is bipartite, with a first hinge 206 and a second hinge 208 connecting a first section 210 to a second section 212. In the embodiment shown, each section 210, 212 is approximately equal in size and represents half of the device 200. In other embodiments, the parts may not be equal in size. As an example, the two parts may comprise approximately ⅓ and ⅔ of the total volume, respectively. In still further embodiments, there may be more than two parts, and such parts may be of equal or different sizes.

Each of the first and second hinges 206, 208 is formed by three ears, with two of the three ears on any given side being formed integrally with one of the sections and the third being formed integrally with the other section. For example, second hinge 208 is formed from two ears 214, 216 of the second section 212 and one ear 218 from the first section 210. In other embodiments, hinges may be formed with greater or fewer numbers of ears. In any event, each of the ears includes an internal bore 220 sized and positioned so as to align when all of the ears are intertwined for closure of the device. Thereafter, a hinge pin 222 (FIG. 3) may be provided to maintain the hinge in the closed position. Other hinge arrangements may also be utilized, including living hinges or non-integral hinges.

FIG. 3 depicts the crimping device 200 in the open condition. In this condition, hinge 206 is intact with hinge pin 222 in place while hinge 208 has its hinge pin (not shown) removed. It will be appreciated that the first section 210 and second section 212 may pivot opened or closed about hinge 206 in this state. In the open condition, the internal cavity 204 is exposed. This internal cavity 204 is in the form of a frustoconical funnel spilling into a cylinder, as further shown in FIG. 3. The funnel 224 includes two main sections, an entry section 226 and an exit section 228. The entry section 226 begins at its end away from the exit section 228 with a relatively large diameter. This larger diameter tapers down toward the exit section 228 to a smaller diameter matching that of the exit section, which is generally cylindrical. It will be appreciated that in the bipartite embodiment shown, the funnel 224 is split equally, with half being formed in each section 210, 212. It will also be appreciated that other configurations, such as where the cavity is offset to one side, may be used. In addition, the cavity may form other configurations, whether geometric or non-geometric, in lieu of the frustoconical funnel spilling into a cylinder shape described and shown herein.

The device 200 itself may be formed from many different materials, including various metals or plastics which are generally suitable for use in a surgical arena. Preferably, the materials are light-weight, robust, and capable of easy sterilization for reuse. Typically, the cavity 204 will be cast with the parts making up the device 200. However, the cavity 204 may also be shaped by other known means, such as drilling, water jetting, or the like. Moreover, and depending on the physical qualities of the material utilized, the internal cavity 204 may be coated with an anti-friction coating to enable reduced friction travel of the stented valve 100, as will be discussed below. The exterior 202 of portions 210, 212 may also be formed with a roughened texture to enhance gripability by those using the device, or may include a separate roughened coating for the same purpose.

As will be discussed, in some embodiments where cold temperatures are utilized, the device 200 may be manufactured from materials with high heat capacities, such as aluminum, titanium, stainless steel, or other materials. Such devices may also be provided with an outer insulation layer. Alternatively, the devices may be formed as a hollow shell, such as of plastic, which is filled with a cold-sustaining gel.

The cavity 204 may also be changed in shape and size via various sleeves or inserts that can be disposed within the cavity. Such inserts would allow the use of a single device for various differed sized or shaped stented valves by sleeving down a relatively large cavity 204. Indeed, in one embodiment, the cavity 204 may be shaped in a manner where it necessarily requires an insert to operate in the manner described herein. For example, the cavity 204 may be entirely cylindrical and may require use of an insert fitted within the cylindrical cavity, the insert typically being a frustoconical funnel with cylinder. Preferably, the insert and cavity include mechanisms to hold the insert in place, such as elements that mechanically interfere and prevent unwanted sliding or separation of the components.

It will be appreciated that the device 200 may also be manufactured from a single component forming both the first section 210 and the second section 212 with a single living hinge between the two sections.

Opening and closing of the device 200 shown in FIGS. 2 and 3 is generally achieved directly, with no mechanical advantage provided. In other embodiments, such as in the embodiment of the device 300 shown in FIG. 4A, provisions may be made to mechanically increase the force available to close the device. As shown in FIG. 4A, the device 300 may include two sections 310, 312 connected by a single hinge 306 which is offset from the sections. The sections may be accompanied by arms 302, 304, forming handles in the form of levers in conjunction with the hinge 306 for added compression strength and ease of handling. The device 300 may also include a locking mechanism 314, such as the selectable physical interference mechanism shown in FIG. 4A. FIG. 4B shows a partial cross-sectional view of FIG. 4A depicting first section 310, funnel 316, and arm 302.

Figure 5:
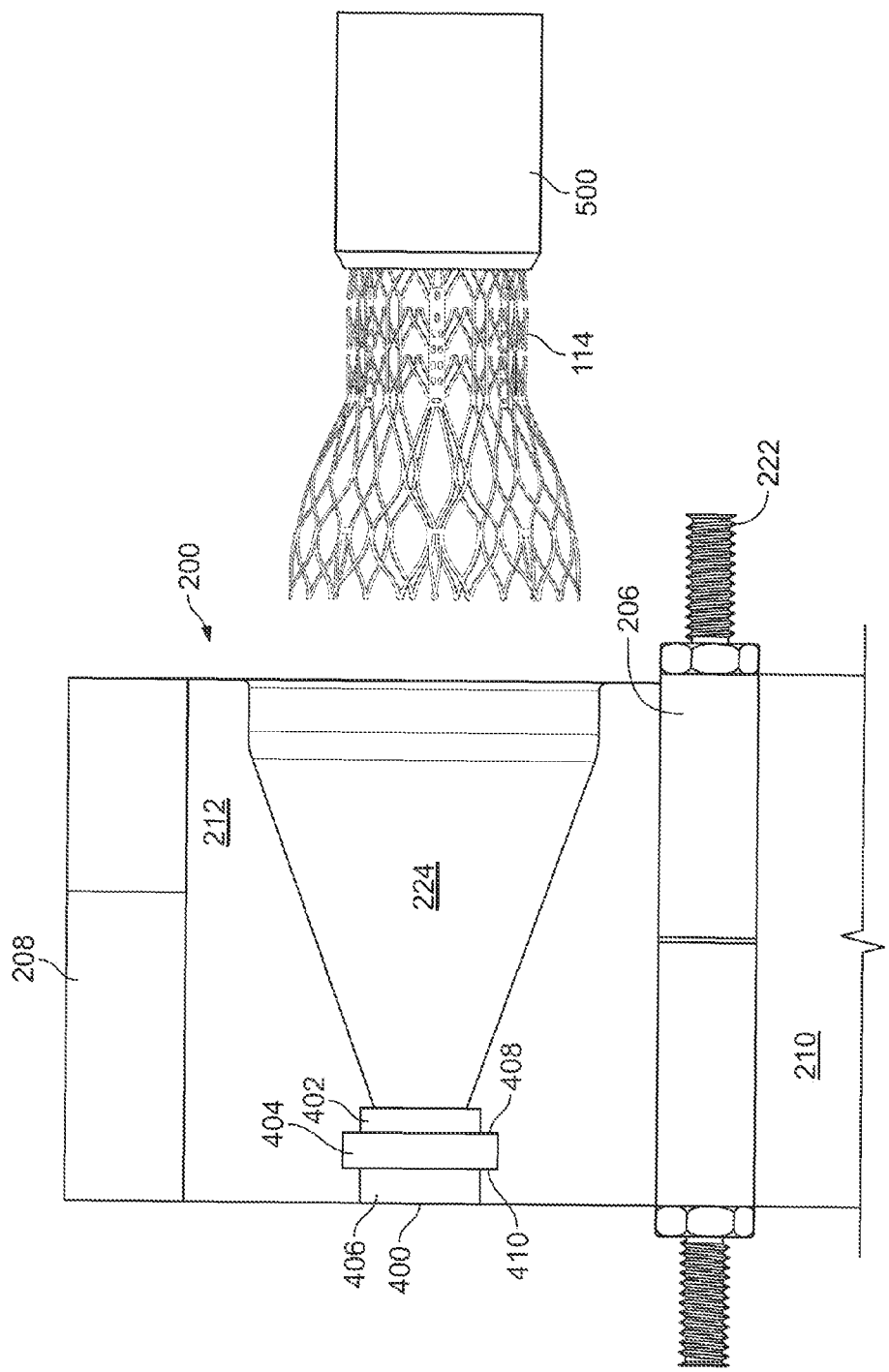
FIG. 5 depicts a perspective view of the bioprosthetic stented valve of FIG. 1 with an attached pusher alongside a device of the type shown in FIG. 2 in an initial step of the method of collapsing the stented valve.

FIG. 5 depicts a stented valve of the type shown in FIG. 1 (with a pusher 500) alongside a device 200 of the type shown in FIG. 3. The device 200 is in the open condition with the first section 210 opened from the second section 212 to expose the funnel 224. Also shown is hinge 206 with the pin 222 in place and a portion of hinge 208 without its pin.

Also shown in FIG. 5, positioned in the cylindrical section 226 of the funnel 224, is a collar 400. The collar shown comprises three sections, a first section 402, second section 404, and third section 406, the second section being between the first and third. Each section 402, 404, 406 is generally cylindrical with varying outside diameters but equal inside diameters. As shown, the outside diameter of the second section 404 is typically greater than that of the other two sections. In this regard, a first shoulder 408 is formed between the first section 402 and second section 404 and a second shoulder 410 is formed between the second section 404 and third section 406. Although not shown in FIG. 5, the internal diameter of the collar 400 may include an orientation portion, such as tab 412, which may later be used to align the collar onto a valve delivery device, as will be discussed in latter portions of this disclosure.

The collar 400 is typically formed from flexible materials such as different types of suitable rubber materials, but may also be fairly rigid and formed from plastics. Preferably such material is biocompatible.

FIG. 5 also depicts a pusher 500 which is used to secure the stented valve and to push the stented valve into the funnel 224. The pusher is generally a cylindrical body of consistent internal and external diameter, and is sized to slide over the cuff 114 of the stented valve to engage same. Preferably, the pusher 500 is formed from relatively stiff material, but should also be fairly flexible as well. Suitable materials include various plastics, which are preferably biocompatible. It will be appreciated that the flexibility allows the pusher 500 to conform somewhat to the shape of the funnel 224 as it travels into the device 200, while the stiffness permits a user "U" to hold the pusher without inadvertently crushing the delicate stented valve 100.

FIG. 5 also generally depicts an initial stage in the loading of stented valve into collar 400. This step, and those that follow, may be performed at various temperatures, such as room temperature. They may also be performed in conjunction with loading devices to be described hereinafter, which employ cold temperature technologies to assist with the crimping and loading process.

As shown in FIG. 5, the pusher 500 is first placed over the cuff 114 of the stented valve. The collar 400 is also loaded onto the cylindrical section 226 of the funnel 224. It will be appreciated that the shapes of the sections 402, 404, 406 of the collar 400 are configured to fit within the cylindrical section 226 without shifting longitudinally along the length of the device 200. Once so placed, the device 200 may be closed such that section 210 meets section 212. The pin (not shown) of the now closed hinge 208 may be inserted, but such is generally not necessary.

Figure 6:
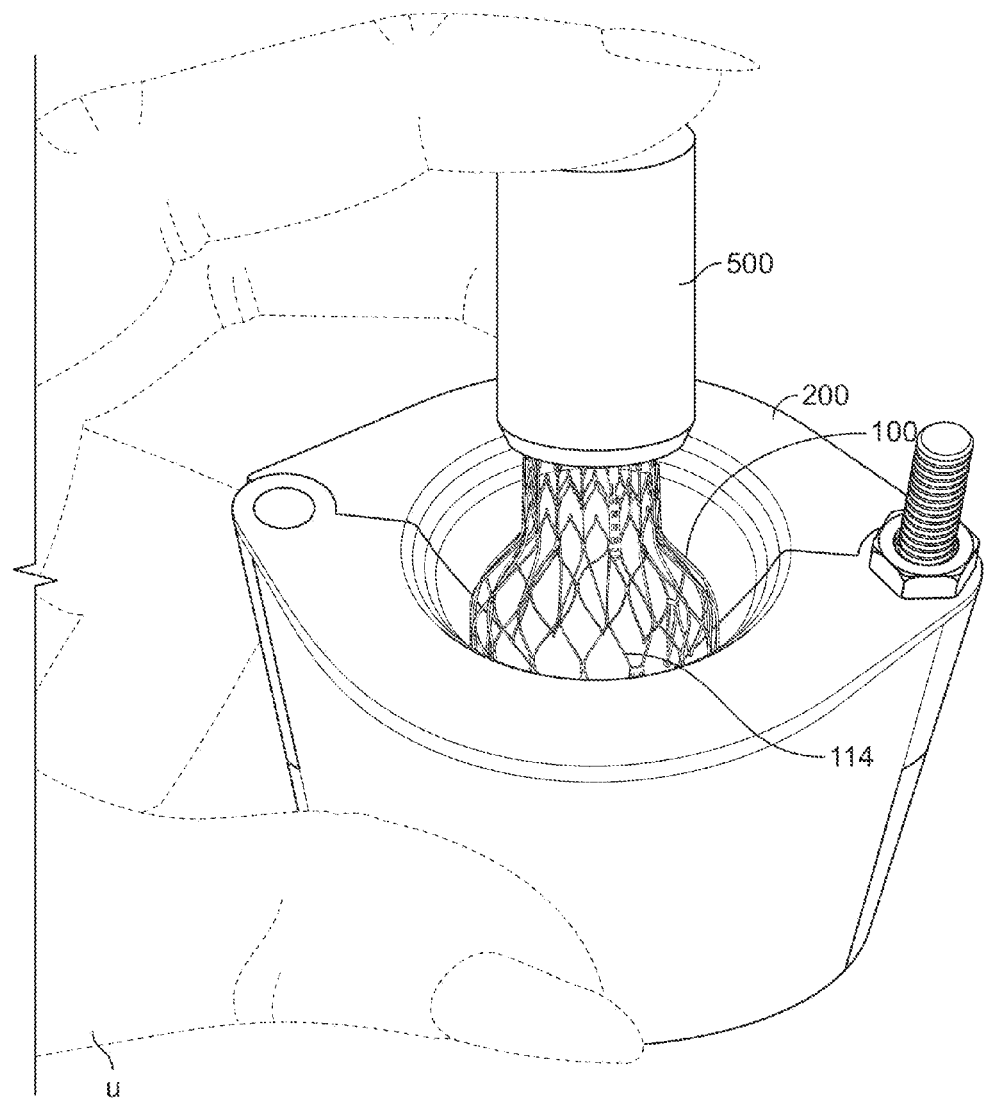
FIG. 6 depicts a further step in the method of collapsing the stented valve depicted in FIG. 5.

FIG. 6 depicts the device 200 in the closed condition. It also shows the stented valve being inserted into the funnel 224 of the device 200 with the aortic section 108 leading. Notably, the pusher 500 is being utilized by the fingers of a user "U" to handle the stented valve 100.

Figure 7:
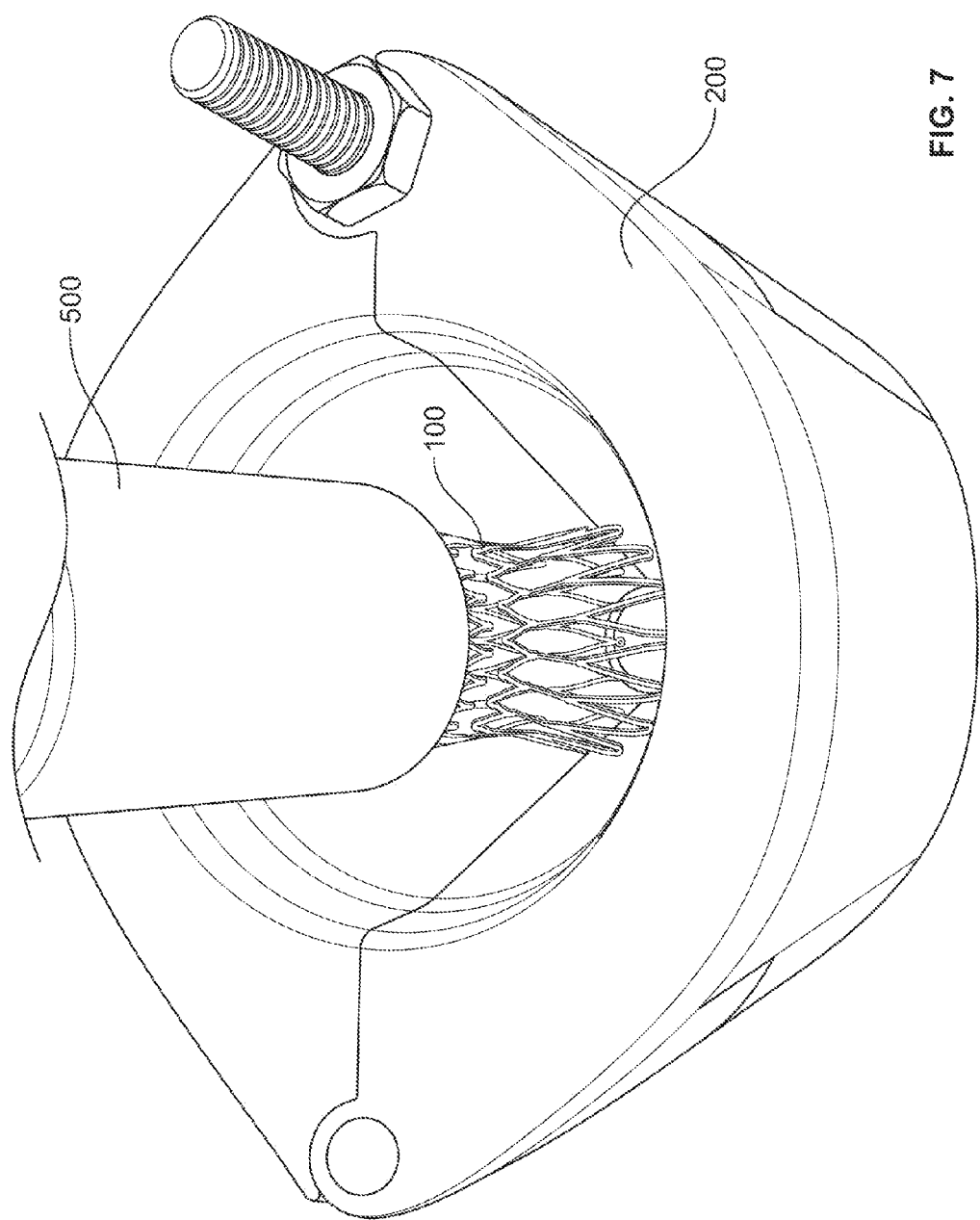
FIG. 7 depicts a still further step in the method of collapsing the stented valve first depicted in FIG. 5.

FIG. 7 depicts the stented valve 100 being inserted a bit further into the device 200. As can be seen, the aortic section 108 is beginning to crimp down to match the diameter of the shaped funnel 224 and eventually of the cylindrical section 226, where it is inserted into the collar 400.

Figure 8:
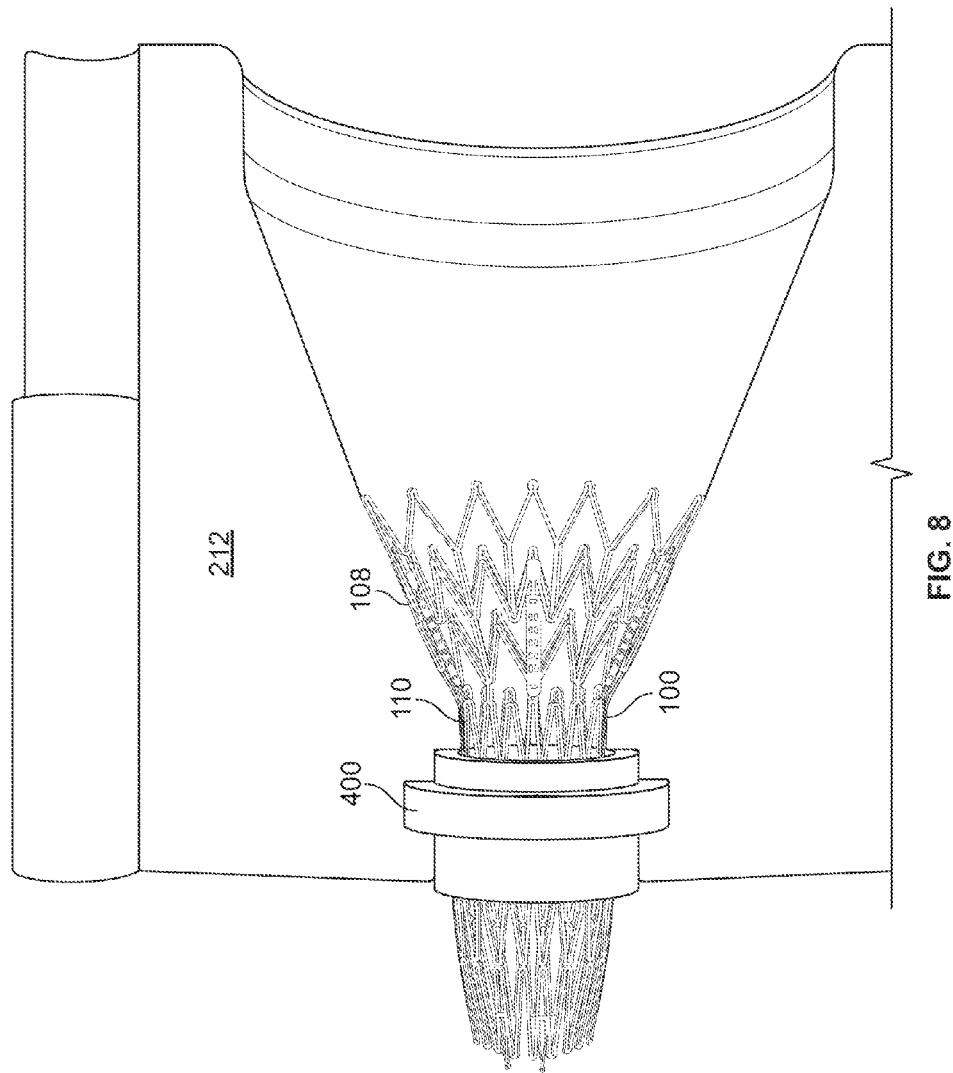
FIG. 8 depicts a stented valve loaded within a collar, both being positioned within an open device for clarity.

FIG. 8 depicts the stented valve 100 fully assembled within the collar 400. For clarity, the device 200 is in the open condition. Typically, the device will remain closed while the stented valve 100 and collar 400 are loaded onto a catheter delivery device, as will be discussed below.

Notably, the stented valve 100 is inserted into the collar 400 only to the point where the collar surrounds the sinus section 110, for which it is sized. This permits the aortic section 108 to remain fairly flared open, but not necessarily to its full diameter. It will also be appreciated that the valve 104 within the stent 102, including the leaflets 112 and commissure lines 116, are designed to be temporarily crimped in this condition during the loading process.

Figure 9:
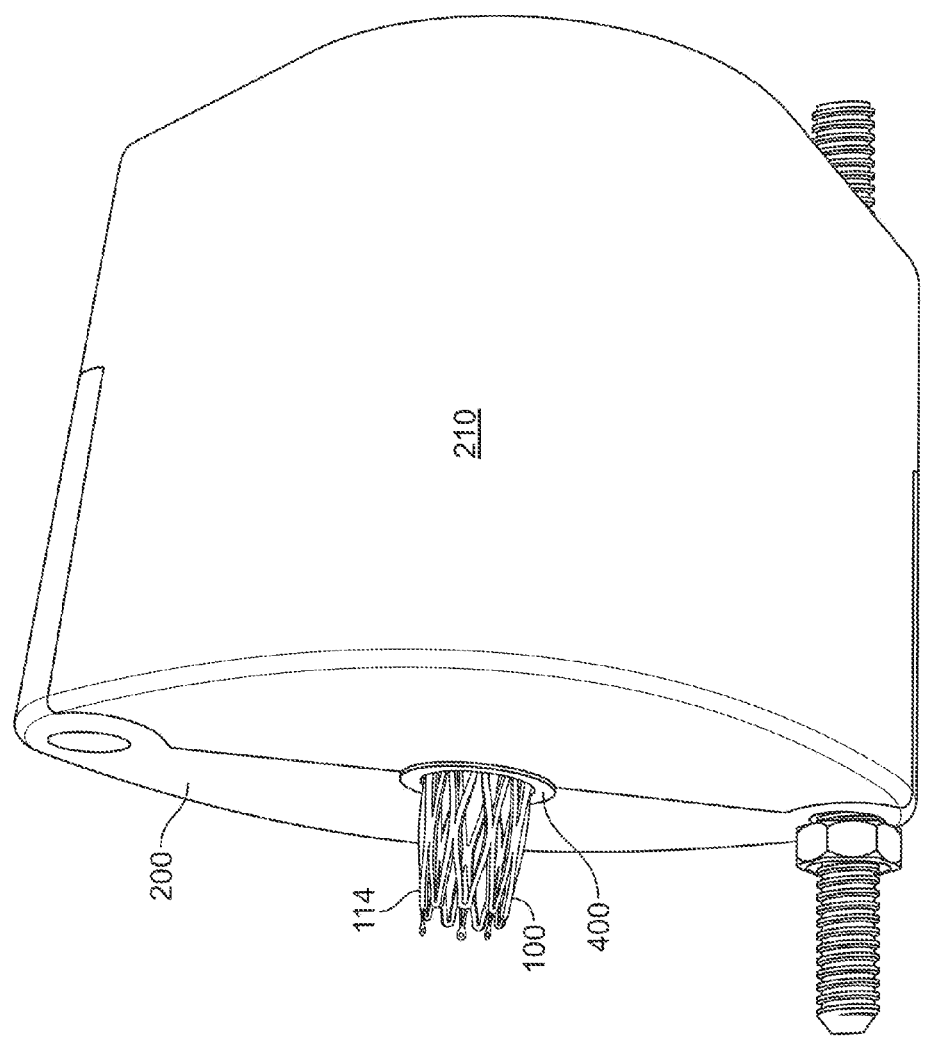
FIG. 9 depicts a perspective view of a stented valve fully inserted within the device of FIG. 8.

FIG. 9 depicts the stented valve 100 in the fully inserted condition within the device 200. In this regard, the cuff 114 of the stented valve 100 protrudes slightly outside of the device 200, just beyond the limits of the collar 400.

Figure 10:
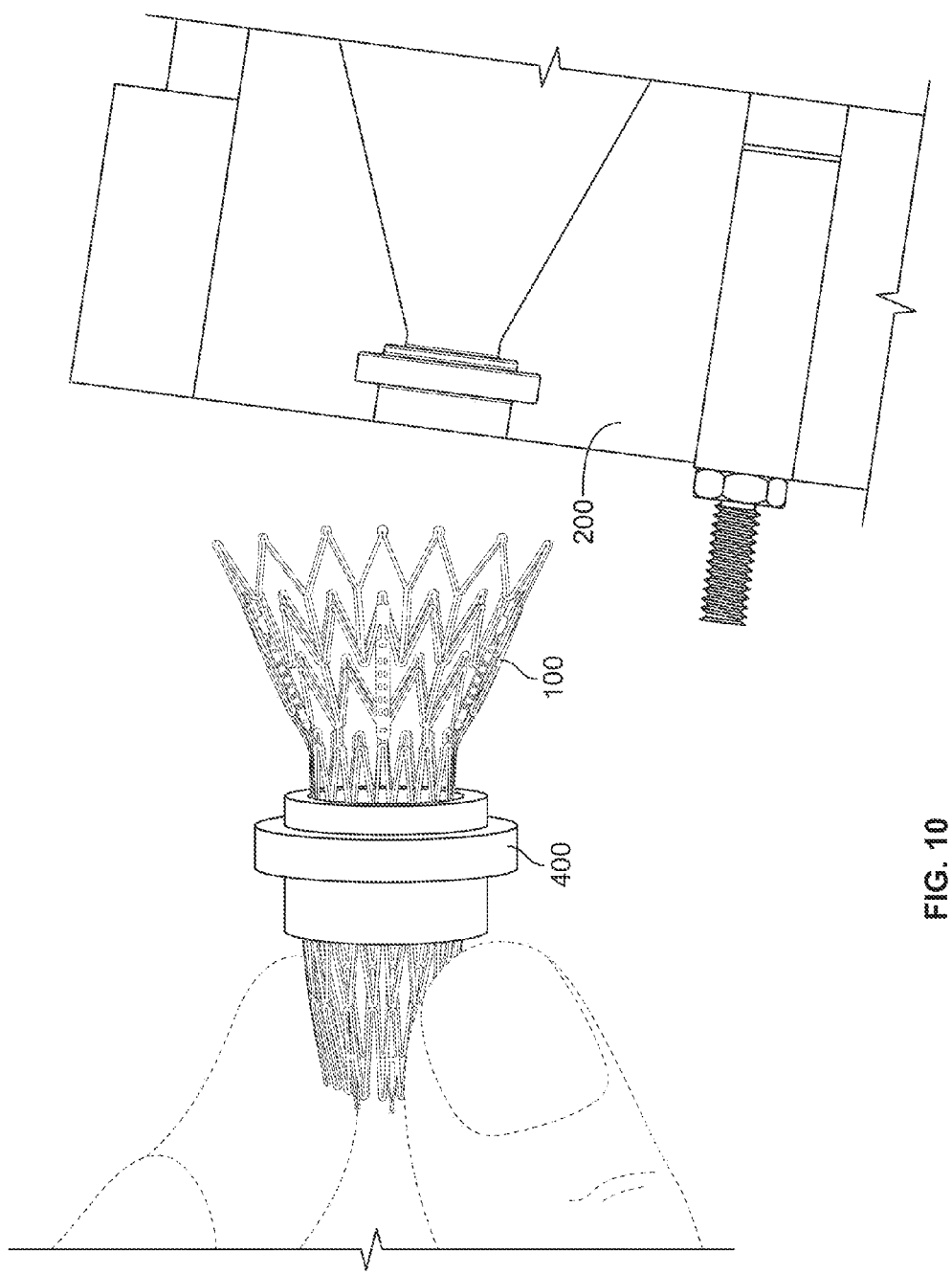
FIG. 10 depicts a perspective view of a stented valve within a collar and removed from the device as a single unit for clarity.

FIG. 10 depicts a user "U" holding the stented valve 100/collar 400 combination for demonstration purposes. The device 200 is shown in the background.

Figure 11:
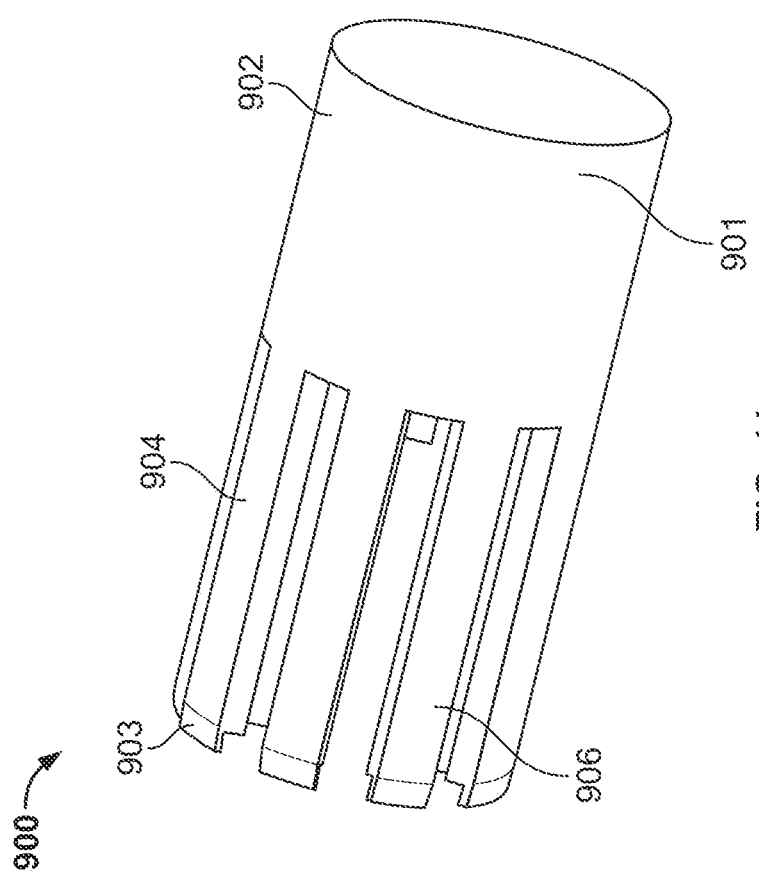
FIG. 11 depicts a perspective view of a further embodiment of a pusher.
Figure 12:
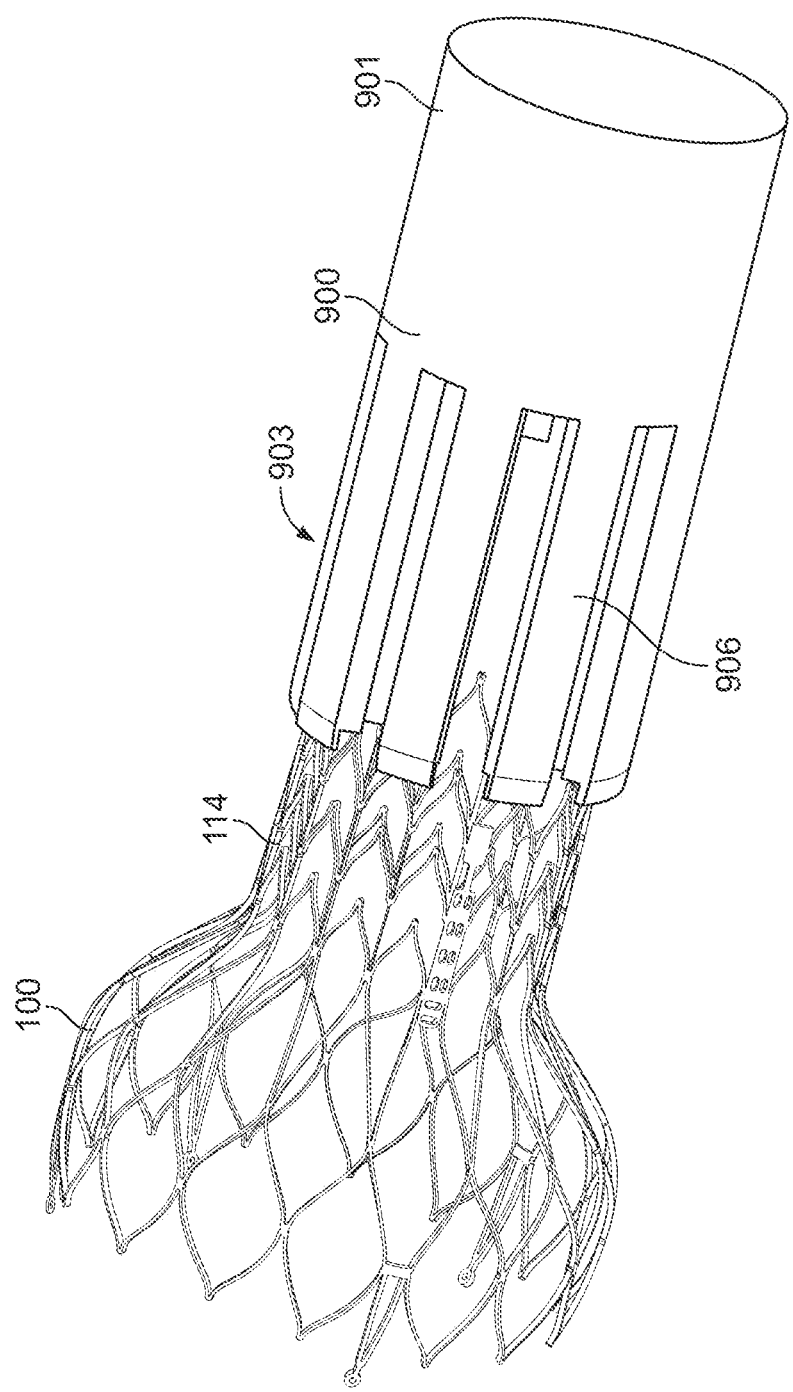
FIG. 12 depicts a perspective view of the pusher of FIG. 12 engaged with a stented valve.

In addition to the method of inserting the stented valve 100 into the device 200 described hereinbefore, additional insertion methods may be utilized. For example, FIG. 11 depicts an alternate embodiment of a pusher 900, which may be utilized for this purpose. In this embodiment, the pusher is still generally cylindrical with consistent internal and external diameter, however it includes a first section 901 and a second section 903. The first section 901 is completely cylindrical and resembles the cylindrical nature of the pusher 500. The second section is also cylindrical, but is configured from separated cantilevered fingers 906. It will be appreciated that the fingers 906 permit the pusher 900 to reduce in diameter as it is inserted, fingers first, into the funnel 224 of the device 200. The fingers are also configured to capture the cuff 114 of the stented valve 100, as shown in FIG. 12.

Due in particular to the fingers 906, which cantilever off the first section 901, the pusher 900 may be configured from materials which are stiffer than those of pusher 500. Even with such stiffer materials, the fingers will reduce in diameter as the pusher is slid within the funnel 224 of the device 200, thus enabling the stented valve 100 to crimp into its smaller diameter while helping to prevent the user from crushing the delicate stent.

Other methods of advancing the stented valve 100 through the device 200 are also provided. One such example is shown beginning with FIG. 13, and includes the use of tethers.

Figure 13:
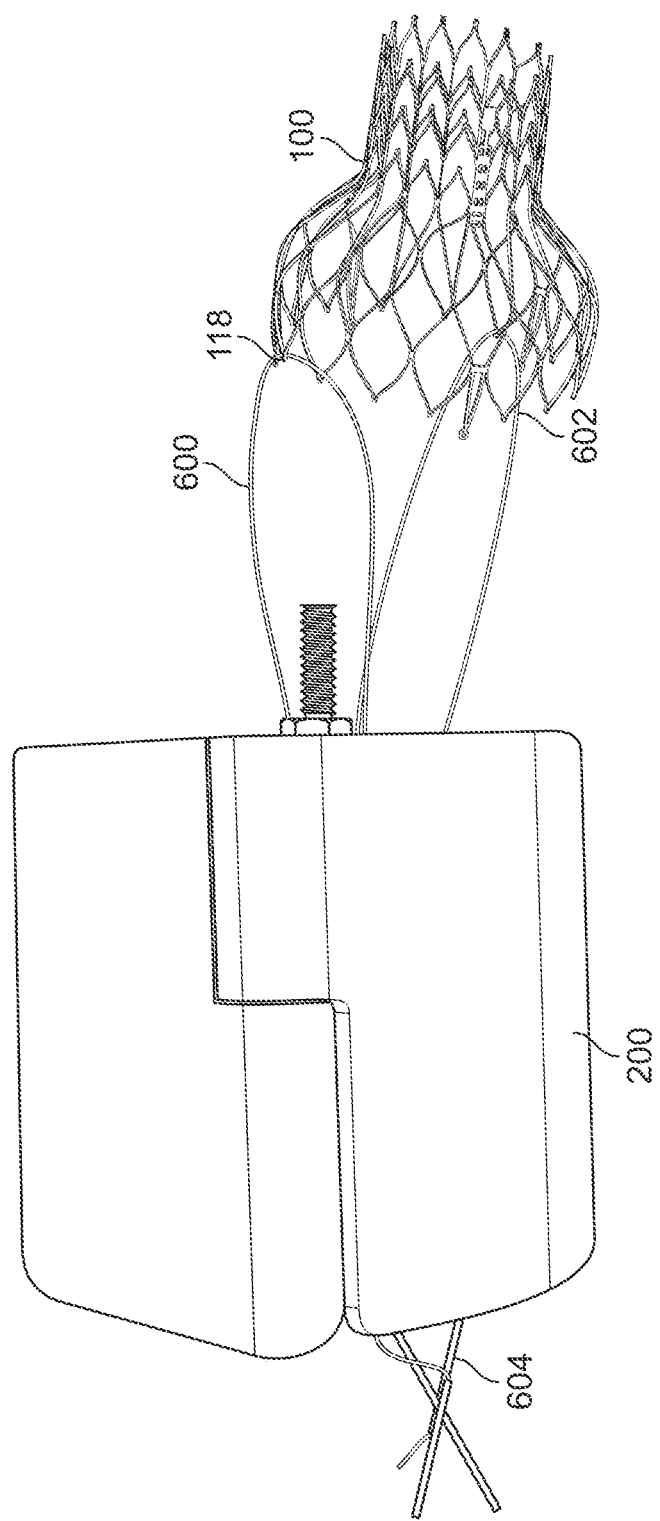
FIG. 13 depicts perspective view of a device for collapsing and loading a heart valve onto a minimally invasive delivery system utilizing a method involving tethers to advance the stented valve.

As shown in FIG. 13, tethers 600 may be attached to the eyelets 118 of the stented valve 100 at a first end 602 of the tethers (all or less than all of the eyelets 118 may be utilized). A second end 604 of the tethers 600 may be threaded into the device 200 and through the cavity 204. The second end 604 of the tethers may then be pulled to bring the stented valve 100 through the device 200. For example, a user may grasp the second end 604 of the tethers to pull the stented valve 100 through the device 200, thus reducing the diameter of the stented valve as it travels through the cavity 204. As in previous embodiments, a collar 400 (not shown in FIG. 13) may be provided in the cavity 204 for positioning around the collapsed stented valve 100.

Figure 14:
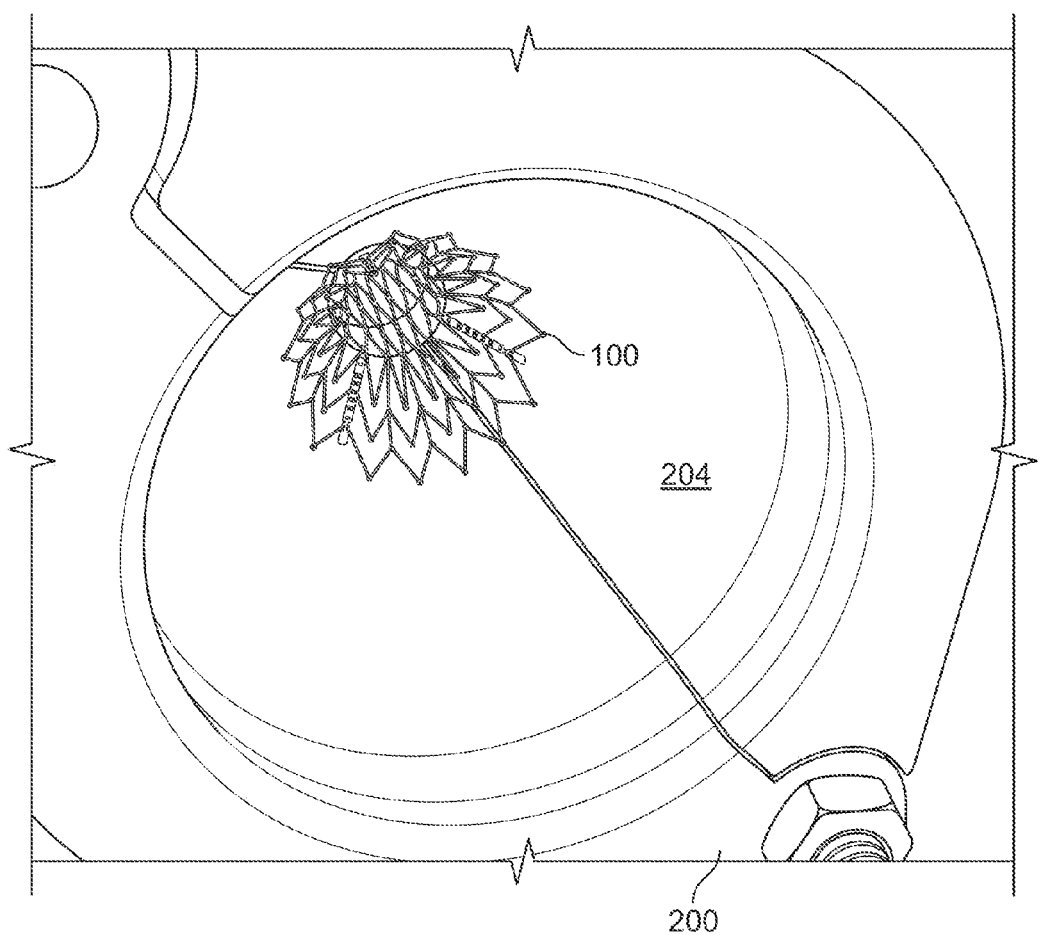
FIG. 14 depicts an internal view of the device with the stented valve inserted therein.

FIG. 14 depicts an end view of the device 200 with the stented valve 100 pulled partially through the cavity 204, without the use of a collar for clarity.

Figure 15:
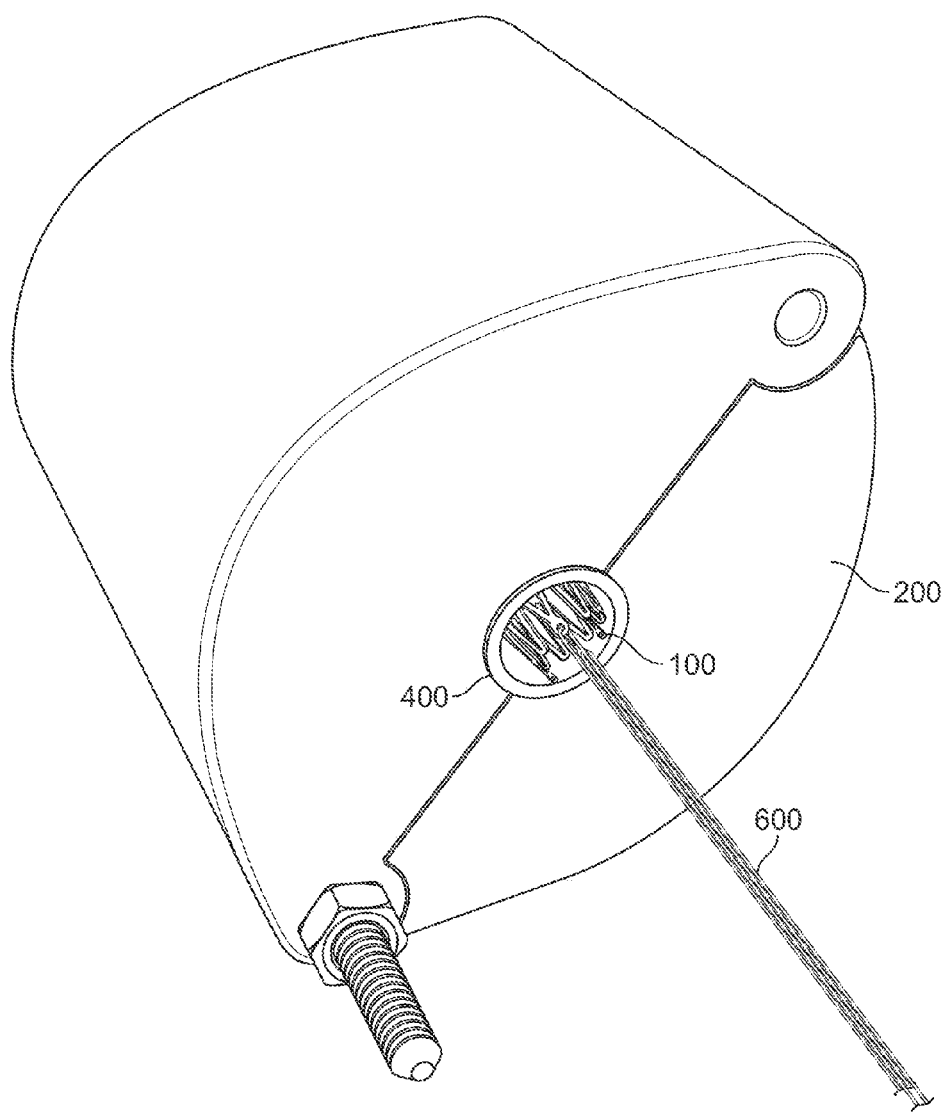
FIG. 15 depicts a perspective view of a step in the method of advancing a stented valve through the device with tethers.
Figure 16:
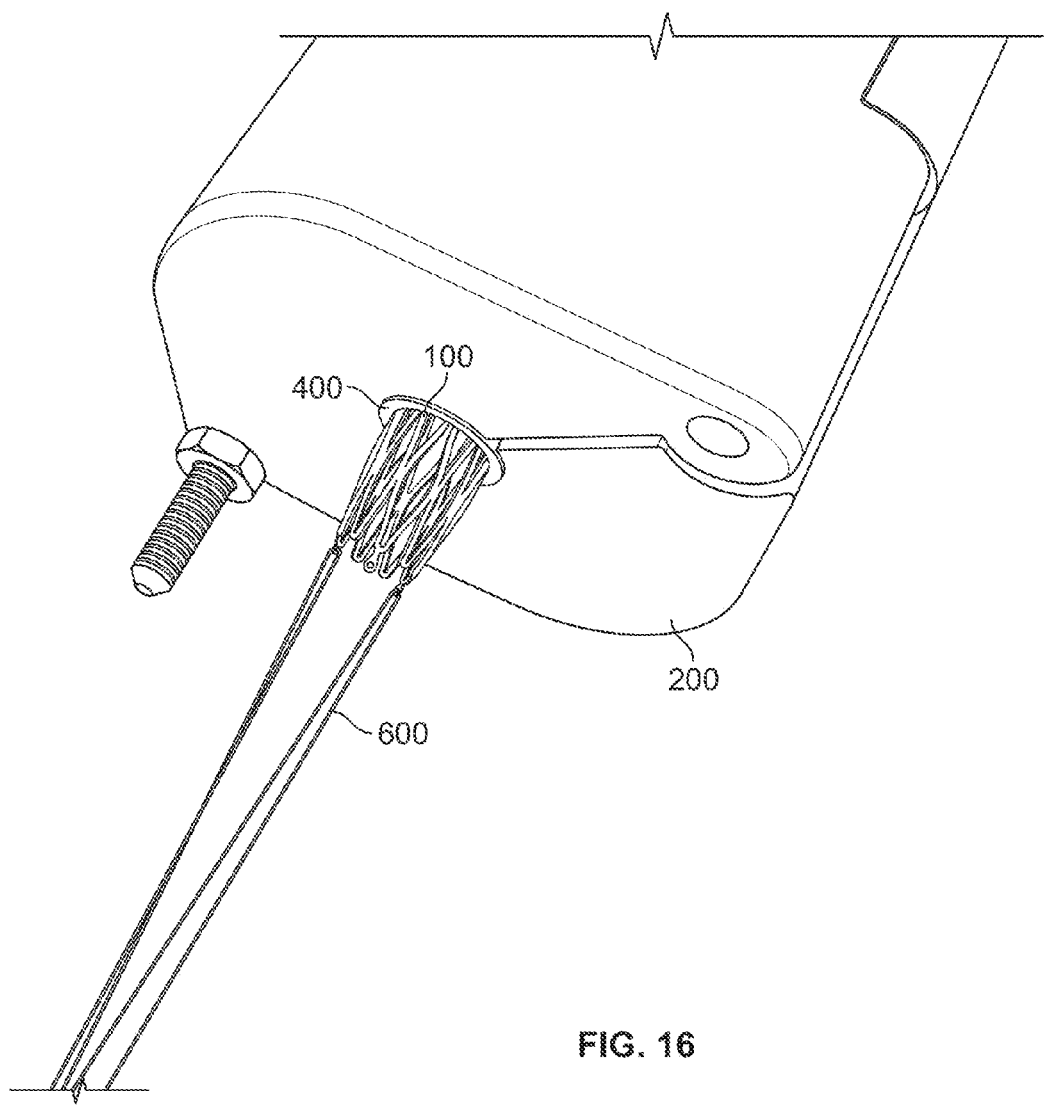
FIG. 16 depicts a perspective view of a further step in the method of FIG. 15.
Figure 17:
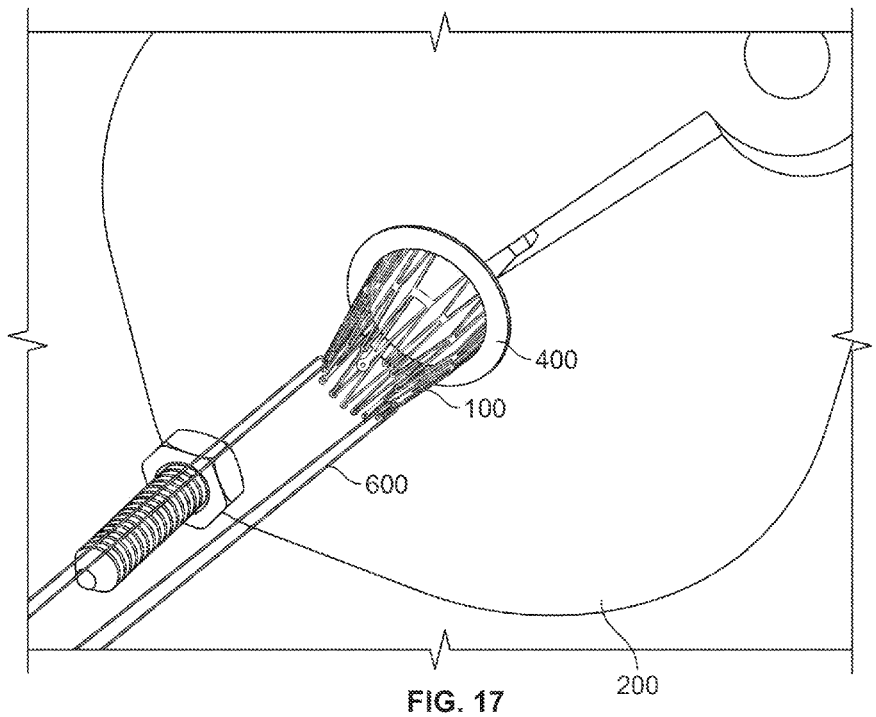
FIG. 17 depicts a perspective view of another step in the method of FIG. 15.

FIGS. 15-17 depict views of the stented valve 100 being pulled through the cavity 204 of the device 200, in various stages along the progression. As shown in FIG. 15, an early stage, the stented valve 100 may need to be "rocked" side-to-side slightly to ensure that it is seated properly within the collar 400. In this regard, the stented valve 100 may be pulled through the device 200 at varying degrees off the main axis through the device 200. It is preferred that such angulations be less than that which would overstress or otherwise compromise the stented valve structure. FIG. 16 depicts a stented valve 100 being pulled straight out of the device 200, with no angulation, in a more advanced stage of the procedure. By FIG. 17, the stented valve 100 is fully seated in the collar 400. Once so seated, the tethers 600 may be removed.

The tethers 600 may be made from any suitable string-like material that is both strong enough to pull the stented valve 100 and thin enough to be attached to the eyelets 118, for example by threading therethrough or by tying. It will also be appreciated that if the tethers 600 are not tied directly to the eyelets 118, they may be attached by other means such as hooks, and in that regard may be thicker than otherwise indicated. Suitable materials for the tethers include stainless steel wire, or other metal wires.

Figure 18:
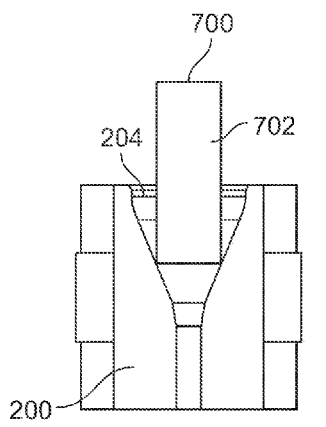
FIG. 18 depicts a diagrammatic view of a telescoping pusher within the device, the pusher in a closed condition.
Figure 19:
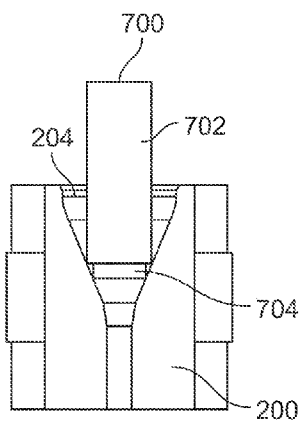
FIG. 19 depicts a diagrammatic view of the telescoping pusher of FIG. 18 within the device, the pusher in a partially advanced condition.
Figure 20:
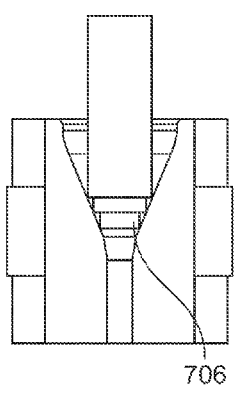
FIG. 20 depicts a diagrammatic view of the telescoping pusher of FIG. 18 within the device, the pusher in a fully advanced condition.

In yet another method of advancing the stented valve 100 through the cavity 204 of the device 200, a telescoping pusher 700 may be provided, as shown in FIGS. 18-20. The telescoping pusher 700 generally operates in a manner similar to pusher 500 shown in FIG. 5, but includes multiple telescoping sections adapted to advance the stented valve 100 through the cavity 204 as the cavity decreases in dimension. For example, as shown in FIG. 18, telescoping pusher (shown without the stented valve for clarity) 700 may advance the stented valve 100 into the cavity 204 only so far as the diameter of the outer element 702 telescoping pusher is less than the cross-sectional dimension of the cavity 204. Once there is interference between the outer element 702 and the cavity 204, a first inner element 704 may extend from within the telescoping pusher 700, as shown in FIG. 19, where the first inner element has a diameter smaller than that of the outer element such that it may advance deeper into the cavity. It will be appreciated that the telescoping pusher 700 may include additional inner elements, such as a second inner element 706 as shown in FIG. 20. As many inner elements as necessary to fully advance the stented valve through the cavity 204 of the device 200 may be provided.

Various devices for advancing the inner elements from the telescoping pusher are known in the art, and may be utilized. Moreover, it will be appreciated that materials utilized for the telescoping pusher 700 may be more rigid than those used for the pusher 500 described previously. This is because of the telescoping nature of the pusher 700, and the inherent "reduction" in diameter through telescoping rather than through bending. Of course, the telescoping pusher 700 may be fairly flexible and preferably is not be completely unyielding.

Figure 21:
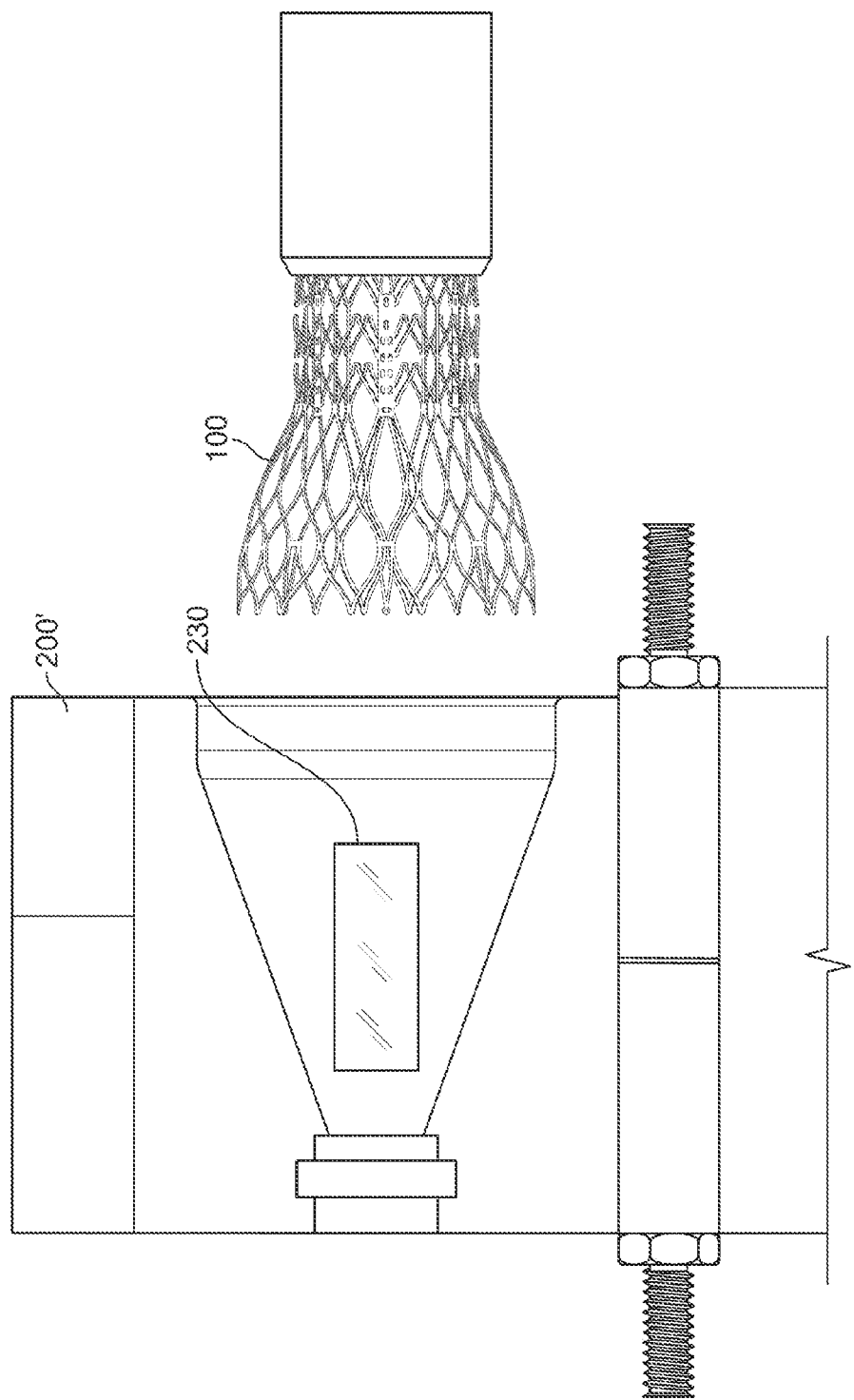
FIG. 21 depicts a perspective view of a device in accordance with further embodiments of the present invention.

Referring back to devices in general, FIG. 21 depicts an alternative embodiment of a device 200a where the device includes a viewing window 230. It will be appreciated that the viewing window 230 enables a user to view the location of the stented valve 100 and advancement mechanism (such as pusher 500) within the cavity 204 of the device 200a. It will also be appreciated that multiple viewing windows 230 of various sizes and dimensions may be utilized. Such windows 230 may be formed from various known materials which are suitable for the surgical arena and are preferably transparent. Translucent materials may also be provided, if desired. The window 230 may be adhered to the device via mechanical or chemical welding. In alternate embodiments, the entire device may be manufactured from transparent or translucent materials, thus avoiding the need for a separate window and enabling full 360 degree viewing through the device.

It is known that catheter systems may be utilized to deliver a stented valve, such as stented valve 100, to the annulus of a compromised native valve within the heart to replace the native valve. In addition to crimping the stented valve 100, devices 200 of the type described herein may also be utilized to assist with loading of the stented valve onto the catheter based minimally invasive delivery system.

Figure 22:
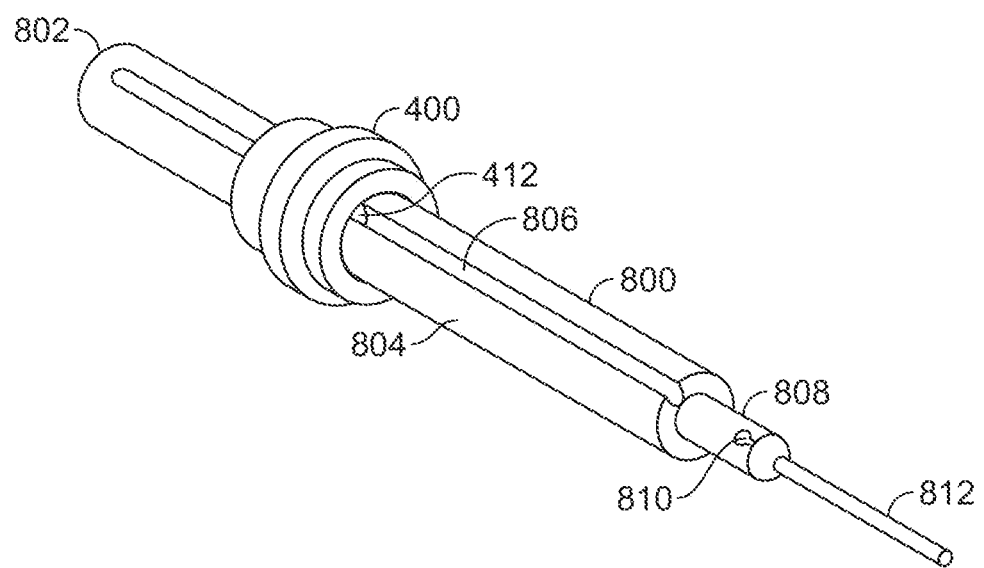
FIG. 22 depicts a perspective view of a portion of a catheter system utilized to deliver a stented valve to the annulus of a compromised native valve in a patient, the catheter including a collar mounted thereon.

A perspective view of a portion of such a catheter 800 is shown in FIG. 22. In the portion shown, the catheter 800 includes a distal end 802, which is the end that ultimately leads the device into the heart. The distal end 802 of the catheter generally forms a cylindrical body 804, and may include a groove 806 extending along its longitudinal axis. Shown in FIG. 22 mounted on the cylindrical body 804 of the catheter 800, is a collar 400. The collar 400 is shown without the stented valve 100 for clarity. In other views, the stented valve 100 will also be shown.

Extending off the cylindrical body 804 of the catheter 800 toward a proximal end thereof (not shown) is a connection member 808. The connection member 808 is also cylindrical, but is of a smaller diameter than the cylindrical body 804. The connection member 808 includes a recess 810 sized and configured to accept an eyelet 118 of a stented valve 100 for securing the valve in the catheter. Finally, extending from the connection member 808 further toward the proximal end (not shown) of the catheter 800 is a wire 812.

Referring back to the collar 400 mounted on the cylindrical body 804 of the catheter 800, it will be appreciated that the tab 412 is located within the groove 806. The tab 412 and groove 806 are sized and configured for such purpose, and are utilized to align the collar 400 onto the catheter 800.

Figure 23:
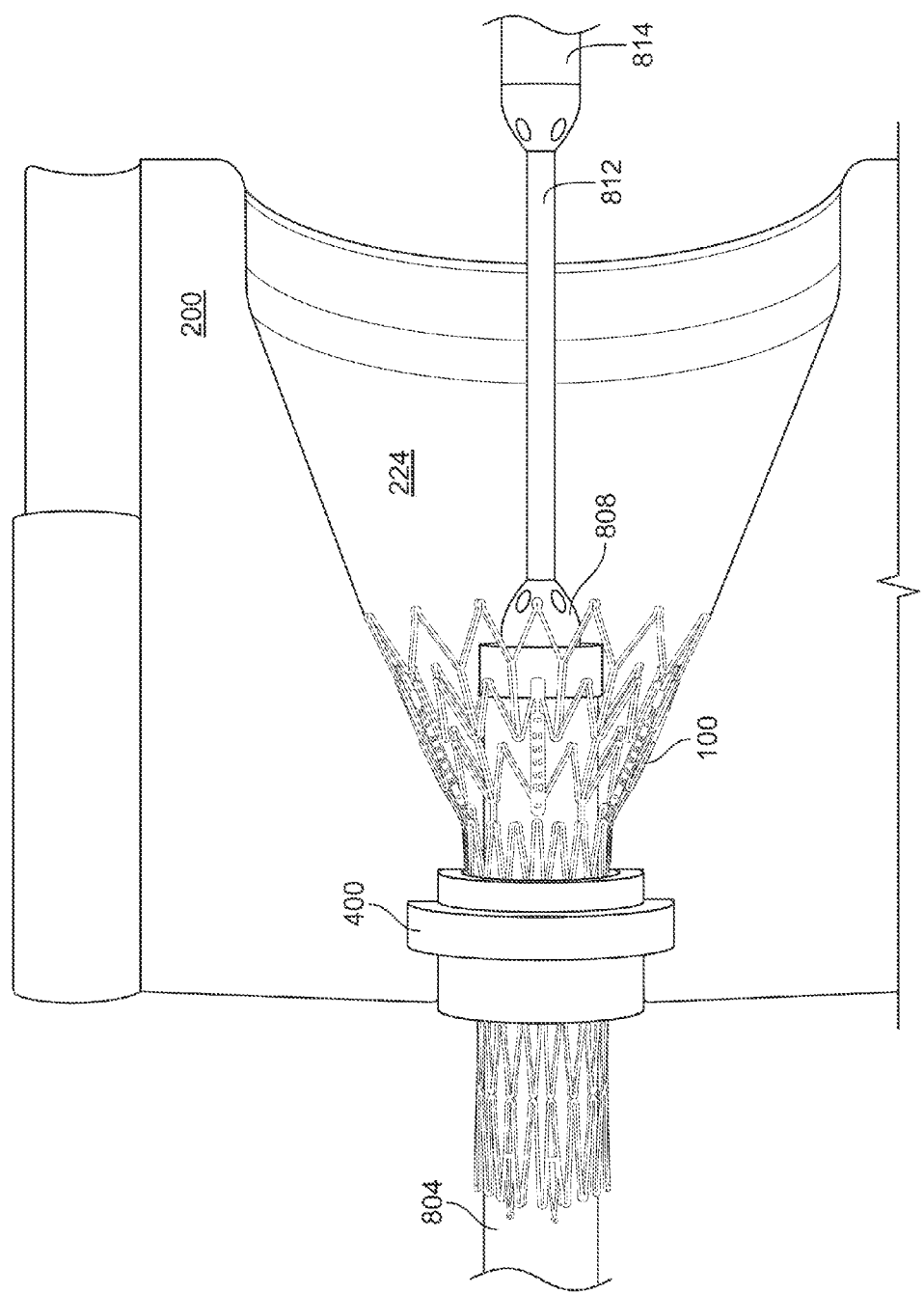
FIG. 23 depicts a perspective view of a portion of the catheter of FIG. 22 inserted within a stented valve in a device, the device being open for clarity.
Figure 24:
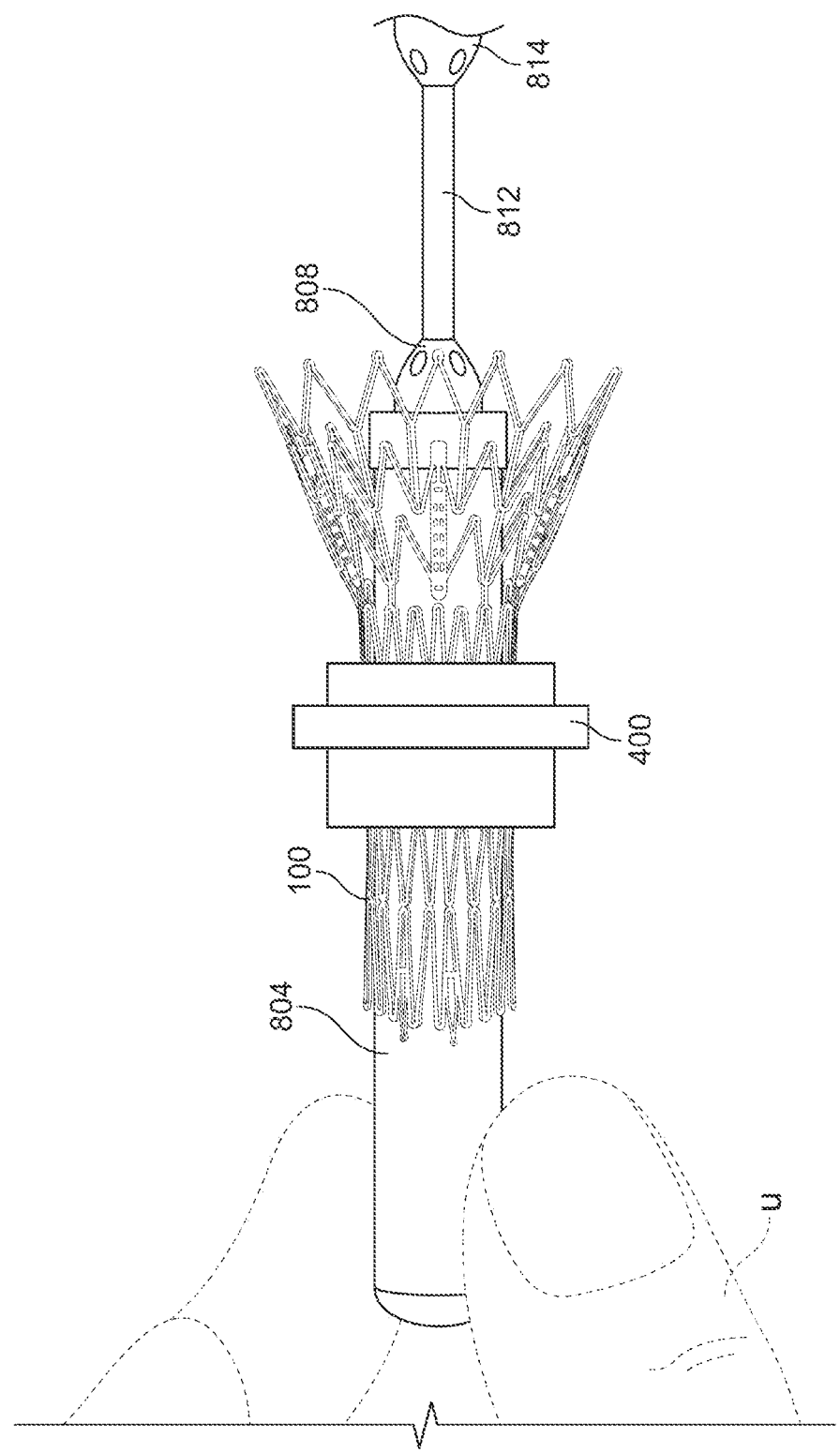
FIG. 24 depicts a perspective view of a portion of the catheter of FIG. 22 with a stented valve and collar mounted thereon.

FIG. 23 depicts a view of the stented valve 100 loaded onto a collar 400 similar to that of FIG. 8 (the device being shown open for clarity), but with the inclusion of a catheter being inserted into the crimped valve. In this regard, it will be appreciated that once the stented valve 100 is crimped within the collar 400, the pusher 500, or other advancement mechanism, may be removed from the device. A catheter 800 may then be inserted into the stented valve 100, distal end 802 first, and from the funnel end 224 of the cavity 204. Once in this position, the device may be opened and the catheter 800, stented valve 100, and collar 400 removed there from as a single unit. Such single unit is shown in FIG. 24.

It will be appreciated that the stented valve 100 may be further loaded onto the catheter 800 by bringing the stented valve and collar to a position over the wire 812 and subsequently drawing the cylindrical body 804, which may be hollow for this purpose, over the aortic section 108 of the stented valve to further crimp the valve and to push the collar 400 off the valve. The cylindrical body 804 is drawn until it meets with a second cylindrical body 814 and fully engulfs the stented valve 100.

As alluded to above, devices of the type described previously may be adapted to take advantage of cold temperatures to assist in the valve crimping and loading process. In such situations, a relatively cold temperature can help lessen the crimping forces that are necessary to crimp the stented valve. In some cases the reduction in required force can be significant.

Accordingly, the device may be made of high heat capacity materials, such as aluminum, stainless steel, titanium, or others, or may be configured with cold-sustaining gel interiors. Such devices can otherwise be generally configured as described with respect to device 200, shown in FIGS. 2-3, for example. The device may be subjected to cold temperatures prior to use, such as by being submerged in a cold bath or placed in a frozen environment. Devices manufactured of high heat capacity materials or cold-sustaining gels are capable of remaining cold, in the range of 0° to 45°, approximately, for a sufficient time to permit the crimping and loading process previously described to be completed. Alternatively, the devices may be coated with an insulating material to assist with extending the time period of reduced temperature and the handling of the device by a user.

Figure 25:
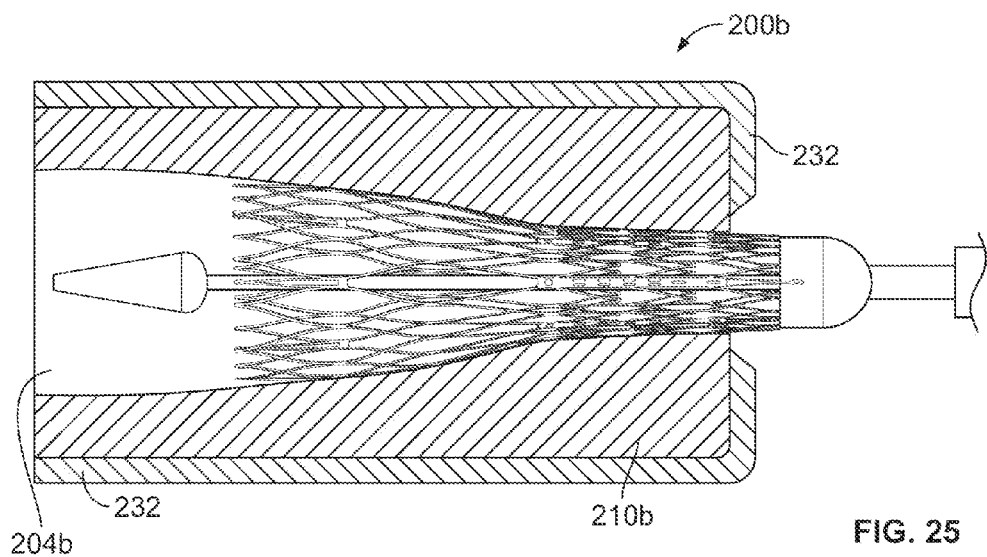
FIG. 25 depicts a cross-sectional view of a device for collapsing and loading a stented valve onto a minimally invasive delivery system, the device utilizing a cold gel core.

Shown in FIG. 25 is a cross-section of one section of a device 200b in accordance with a further embodiment of the present invention, inclusive of insulating material. Device 200b is configured much like device 200 shown in FIGS. 2 and 3, and therefore contains a cavity 204b in the general shape of a frustoconical funnel spilling into a cylinder in section 210b thereof. In addition, device 200b includes an outer insulation layer 232. The outer insulation layer serves to insulate the device 200b as well as to provide protection for a user grasping the cold device. Suitable insulation materials include low thermally conductive materials such as polymer foam or fabric cloth. It will be appreciated that although not shown, the other sections of the device 200b (for example, section 212b of a two-section device), may also be provided with an insulation cover.

Figure 26:
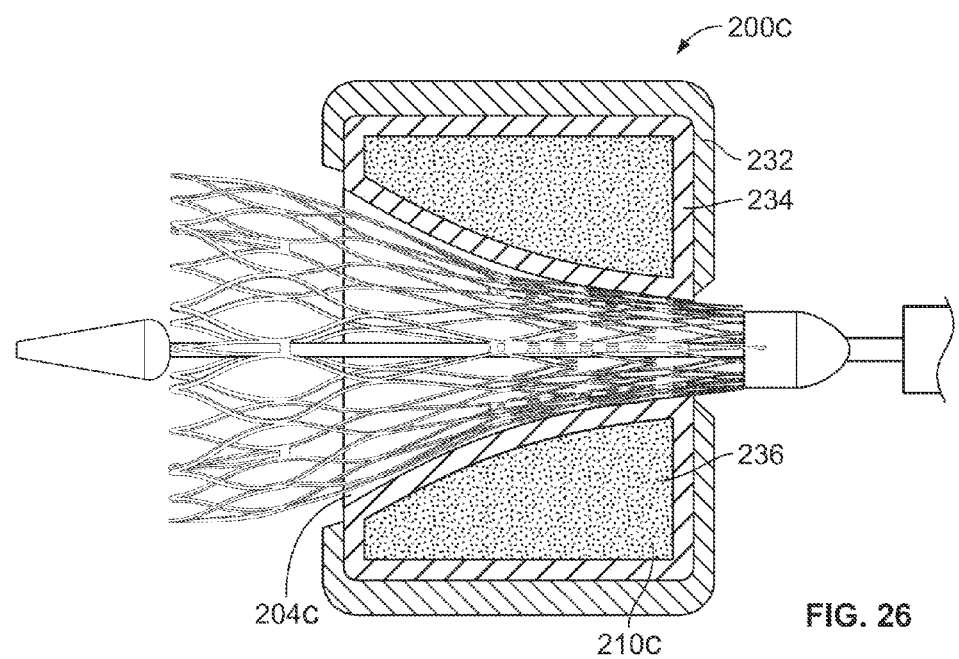
FIG. 26 depicts a cross-sectional view of a device for collapsing and loading a heart valve onto a minimally invasive delivery system, the device utilizing a cold gel core.

Other devices for maintaining a decreased temperature are also contemplated. A cross-sectional view of one section of such a device 200c is shown in FIG. 26. In this device, the sections, for example section 210c shown, may comprise an outer insulation layer 232 covering a structural layer 234 which is filled with a gel 236. The outer insulation layer may be as provided above, and may be configured from low thermally conductive materials such as polymer foam or fabric cloth. The structural layer may be formed from many different materials, such as plastics and metals. Such materials are typically sufficiently rigid for the intended purpose of shaping the cavity 204c and outer portions of the section, and do not necessarily have to be high heat capacity materials. The gel 236, provided within the structural layer 234, may be configured from cold-sustaining gels, such as those conventionally provided in commercial ice packs, which are often made from non-toxic materials. The gel 236 may be placed inside the structural layer 234 during the manufacturing process by use of a small bore (not shown) that is later welded, such as through metal welding or chemical welding, or otherwise closed.

Another method of providing a cold-temperature device is to freeze a device, such as device 200 manufactured from a heat retaining material, with the endothermic reaction of ammonium nitrate and water. Other suitable materials in lieu of ammonium nitrate include calcium chloride and ammonium chloride. One process for achieving sufficient cooling of the cavity 204 involves filling the cavity with water and sealing the cavity. Ammonium nitrate or other suitable chemical can then be released within the sealed off cavity 204. After a sufficient time for the reaction, the cavity is cooled and the seal may be removed to expose the cavity for use. Of course, it is preferred that reliable sealing techniques be utilized.

Any of the devices 200, 200a, 200b, 200c described herein can be provided as non-split devices. Such devices therefore would not be configured from sections 210, etc., but would be wholly intact and complete with a formed cavity. In particular, devices 200b and 200c of FIGS. 25 and 26, respectfully, because of the advantages of reduced temperature use, may be configured as such. With the reduction of temperature provided through these devices, the stented valve 100 may simply be pulled or pushed through the cavity 204 for crimping and loading, without the need for mechanical force to crimp.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A method of loading a stented bioprosthetic valve onto a delivery system, the method comprising:
    crimping the stented bioprosthetic valve from a first condition having a first diameter to a second condition having a second diameter, the second diameter smaller than the first diameter, the crimping being achieved by advancing the stented bioprosthetic valve through a device having a tapered internal cavity, the taper advancing from a first dimension to a second dimension, the second dimension being smaller than the first;
    inserting the stented bioprosthetic valve into a collar having a constant internal diameter;
    and loading the collar and the bioprosthetic valve onto the delivery system by inserting at least a portion of the system into the collar.

2. The method of claim 1, wherein the inserting of the stented bioprosthetic valve into the collar is performed after the crimping step.

3. The method of claim 2, wherein the inserting of the stented bioprosthetic valve into the collar is performed simultaneously with at least a portion of the crimping step.

4. The method of claim 1, further comprising cooling the device.

5. The method of claim 1, wherein the device is comprised of an outer structural shell filled with a cold-sustaining gel.

6. The method of claim 1, wherein the device includes an insulating exterior component.

7. The method of claim 1, wherein the device comprises a first section and a second section separable from the first section, the first section and the second section together at least partially enclosing the internal cavity.

8. The method of claim 7, wherein the first section and second section fully enclose the internal cavity.

9. The method of claim 7, wherein the first section and the second section are movable between a first position at least partially enclosing the internal cavity and a second position wherein the cavity is fully exposed.

10. The method of claim 1, wherein the internal cavity is shaped as a frustoconical funnel spilling into a cylinder, the frustoconical funnel defining the first dimension at an insertion portion of the device and defining the second dimension adjacent the cylinder, the cylinder defining the second dimension at an exit portion of the device.

11. The method of claim 1, wherein the collar has a varying outside diameter configured to fit within the first and second sections, such that the collar is constrained from movement along an axis extending in a direction between an insertion portion and an exit portion of the device.

12. The method of claim 1, wherein the crimping steps is performed using a pusher that pushes the stented bioprosthetic valve through the device.

13. The method of claim 1, wherein the crimping steps is performed using a tether that pulls the stented bioprosthetic valve through the device.

14. The method of claim 1, wherein the collar comprises an orientation portion to align the collar on the delivery system.

15. The method of claim 1, wherein the first section comprises a high heat capacity metal.

16. The method of claim 1, wherein the inner cavity defines a first internal volume, and the device comprises a sleeve extending within the internal cavity, the sleeve having an internal space that defines a second internal volume smaller than the first internal volume.

* * * * *